United States Patent [19]
York, Jr.

[11] Patent Number: 4,464,385
[45] Date of Patent: Aug. 7, 1984

[54] TREATMENT OF DIABETIC COMPLICATIONS WITH HYDANTOINS

[75] Inventor: Billie M. York, Jr., Fort Worth, Tex.

[73] Assignee: Alcon Laboratories, Inc., Fort Worth, Tex.

[21] Appl. No.: 368,629

[22] Filed: Apr. 15, 1982

[51] Int. Cl.³ ................. A61K 31/415; C07D 491/107
[52] U.S. Cl. ................................ 424/273 R; 548/309; 549/401
[58] Field of Search ...................... 548/309; 424/273 R

[56] References Cited

U.S. PATENT DOCUMENTS

| | | | |
|---|---|---|---|
| 2,683,718 | 7/1954 | Dornfeld | 548/309 |
| 2,716,648 | 8/1955 | Jules et al. | 548/308 |
| 3,349,124 | 10/1967 | McLamore | 260/553 |
| 3,532,744 | 10/1970 | Fletcher | 548/308 X |
| 3,821,383 | 6/1974 | Sestanj et al. | 424/258 |
| 4,117,230 | 9/1978 | Sarges | 548/309 |
| 4,127,665 | 11/1978 | Sarges et al. | 424/273 R |
| 4,130,714 | 12/1978 | Sarges | 548/309 |
| 4,147,795 | 4/1979 | Sarges | 424/273 R |
| 4,147,797 | 4/1979 | Kelbaugh et al. | 424/273 R |
| 4,181,728 | 1/1980 | Sarges et al. | 424/273 R |
| 4,181,729 | 1/1980 | Sarges et al. | 424/273 R |
| 4,200,642 | 4/1980 | Schnur | 424/272 |
| 4,209,630 | 6/1980 | Sarges | 548/309 |
| 4,307,108 | 12/1981 | Belletire et al. | 424/274 |
| 4,327,107 | 4/1982 | Cale, Jr. | 424/273 R |

FOREIGN PATENT DOCUMENTS 1135915 9/1962 Fed. Rep. of Germany ...... 548/309

OTHER PUBLICATIONS

Kador, P., et al., *Docum. Ophthal. Proc. Series*, 18, 117-124, (1979).
Kador, P., et al., *Invest. Ophthalmol. Vis. Sci.*, 19, 980-982, (1980).
Kador, P., et al., *Analytical Biochemistry*, 114, 53-58, (1981).
Conant, J., *The Chemistry of Organic Compounds*, Macmillan, New York, 1939, p. 264.
McCown, W., et al., *JACS*, 64, 689, (1942).
Kuhn, W., *Org. Synthesis*, Coll. vol. 2, 447, (1943).
Fletcher, T., et al., *J. Org. Chem.* 25, 1342-1348, (1959).
Pan, H., et al., *J. Med. Chem.*, 7, 31-38, (1964).
Pan, H., et al., *J. Med. Chem.*, 10, 957-959, (1967).
Bavin, P., *Org. Synthesis*, Coll. vol. 5, 30, (1973).
Granoth, I., et al., *J. Org. Chem.* 40, 2088-2091, (1975).
Stewart, M., et al., *J. of Neurochemistry*, 14, 1057-1066, (1967).
Sprinzak, *JACS* 80, 5449, (1958).
Goodson, *J. Org. Chem.*, 25, 1920, (1960).
Fletcher, *Chem. & Indus.*, Feb. 11, 1961, p. 179.
Parry, *JACS*, 4049-4054, (1965).
Prendergast, *J. of Biochem.* 25, 1282, (1975).
McGilvey, *Biochemistry, A Functional Approach*, pp. 631-632, Saunders, Philadelphia, PA, (1970).

*Primary Examiner*—Richard A. Schwartz
*Attorney, Agent, or Firm*—Fitch, Even, Tabin & Flannery

[57] ABSTRACT

6-Methythio and 6-methylsulfinyl spiro-chroman-imidazolidine diones useful in the treatment of complications arising from diabetes mellitus.

4 Claims, No Drawings

TREATMENT OF DIABETIC COMPLICATIONS WITH HYDANTOINS

This invention relates to new and useful hydantoin derivatives in medicinal chemistry. This invention particularly relates to 6-methylthio and a 6-methylsulfinyl (also known as 6-methylsulfoxide) spiro-chroman-imidazolidine diones, which are useful in the treatment of complications arising from diabetes mellitus such as cataracts, neuropathy, retinopathy and nephropathy.

Aldose reductase inhibitors inhibit the activity of the enzyme aldose reductase. Aldose reductase is mainly responsible for the reduction of aldoses to polyols, e.g., glucose and galactose to the polyols sorbitol and galactitol. Accumulations of galactitol and sorbitol in diabetic subjects cause diabetic complications including ocular complications. Polyols in the eye lead to cataracts and loss of lens clarity. Hence, aldose reductase inhibitors reduce the ability of aldose reductase to produce polyols which lead to the formation of cataracts.

K. Sestanj et al. in U.S. Pat. No. 3,821,383 describes 1,3-dioxo-1H-benz-[d,3]-isoquinoline-2(3H)-acetic acid and derivatives thereof as aldose reductase inhibitors. The search for effective antidiabetic agents to prevent or arrest chronic complications such as cataracts, neuropathy and retinopathy has revealed that particular spirohydantoin compounds are useful as aldose reductase inhibitors.

U.S. Pat. No. 4,117,230 describes a series of spiro-hydantoin compounds which include the 6-fluoro and 6,8-dichloro derivatives of spiro-chromanimidazolidines. U.S. Pat. No. 4,117,230 shows that when alkyl substitutions larger than methyl were made in the 6-position of the spiro-(chroman-4,4'-imidazolidine)-2',5'-dione moiety, activity declines, the most active being the unsubstituted 6-position in that series. One would believe, therefore, that a bulky methylthio group would have less activity than the 6-methyl and/or 6-ethyl derivative.

U.S. Pat. No. 4,130,714 describes enhanced activity of specific dextrotatory spiro-hydantoin compounds such as d-6-fluoro-spiro-[chroman-4,4'-imidazolidine]-2',5'-dione and d-6'-fluoro-spiro[imidazolidine-4,4'-thiochroman]-2,5' dione in preventing chronic diabetic complications.

U.S. Pat. Nos. 4,181,728 and 4,181,729 describe spiropolycyclicimidazolidinedione derivatives and phenyl or phenoxy substituted spiro-imidazolidinedione derivatives, respectively, which are useful to inhibit the enzymatic reduction of aldoses to prevent or reduce harmful and unwanted accumulations of polyols in the lens and retina of the eye.

In accordance with the present invention it has been found unexpectedly that spiro-(6-methylthiochroman-4,4'-imidazolidine)-2',5'-dione and spiro-(6-methylsulfoxide-chroman-4,4'-imidazolidine)-2',5'-dione may be employed as aldose reductase inhibitors for the control and prevention of sorbitol levels in the sciatic nerve and lens of diabetics and may be employed to reduce galactitol levels in the lens of galactosemic subjects with the resulting control of diabetic complications including diabetic cataracts, neuropathy, retinopathy and nephropathy. It was found in vivo that the methylthio group can be converted to the methylsulfinyl derivative by membrane bound cytochrome containing oxidoreductase enzymes common to the liver, kidney and lung. It was found that the resulting methylsulfinyl derivative lacked the activity of the methylthio derivative and established in situ a dynamic buffering system, ultimately according to a reduced concentration of each species, thereby reducing the overall toxicity potential. The more bulky methylsulfoxide derivative was shown itself in vitro to inhibit human placental aldose reductase. These findings indicate the biotransformation of the methylthio group to the methylsulfoxide derivative leads to a mixed species, each having desired activity. It is believed that the plasma half-life of the total drug species will be prolonged by an intermediary metabolism due to a reductive recycling of the methylsulfoxide metabolite by thioredoxins and/or glutaredoxins to the more active methylsulfide drug species. Therefore, the methylsulfoxide upon oral administration will undergo subsequent metabolic reduction to the more active methylthio derivative. Surprisingly, however, with its buffering and reduced toxicity advantages the methylthio compound exhibited a potency similar to the resolved 6-fluoro compound described in U.S, Pat. No. 4,130,714.

The 6-methylthio-spiro-(chroman-4,4'-imidazolidine)-2',5'-dione,

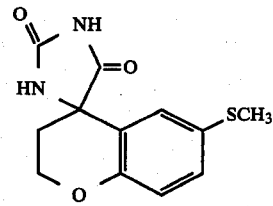

and
6-methylsulfoxide-spiro-(chroman-4,4'-imidazolidine)-2',5'-dione,

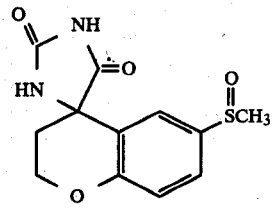

may be prepared from the following synthesis.

PREPARATION A

With caution 210 g (1.5 moles) of 4-methylthiophenol and 120 g (3.0 moles) of sodium hydroxide in 200 ml of water was slowly added to 163 g (1.51 mole) of 3-chloropropionic acid. The mixture was heated to reflux for 20 hours. After reflux the unreacted 4-methylthiophenol was removed by distillation and the hot reaction mixture poured with stirring onto ice and concentrated hydrochloric acid. The slurry was filtered and collected on a buchner funnel. The wet mass was added to a solution of 300 ml of 1% sodium hydroxide solution and 300 ml of ethyl acetate. The resulting mixture was poured into a one liter separatory funnel, and after extraction with 1% sodium hydroxide, the aqueous layer was drawn off. The organic layer was extracted a second and third time with 1% sodium hydroxide. The extracts were added to a two liter separatory funnel, acidified with concentrated hydrochloric acid after the ethyl acetate was layered on. The organic extract was collected and dried over anhydrous Na₂-

SO$_4$, and two heaping teaspoons of activated charcoal were added to the yellow solution. Filtering removed insolubles and the resulting light yellow solution was reduced to a white sticky solid using a rotary evaporator at 65° C. and reduced pressure. Recrystallization from hot benzene yields white needles of 3-(4-methylthiophenoxy)-propionic acid with a melting point of 129°–131° C. (uncorrected).

PREPARATION B

3(4-Methylthiophenoxy) propionic acid (17 g 0.08 mole) was added to a dry one liter flask. Dry benzene (300 ml) was added to the flask along with granular P$_2$O$_5$ (50 g). The mixture was refluxed for approximately 20 hours, whereupon the reaction mixture was cooled, the benzene decanted, and residual solid extracted four times with dry benzene. The benzene solutions were combined and extracted with aqueous sodium carbonate followed by a distilled water wash. The benzene was dried over anhydrous Na$_2$SO$_4$. The dried benzene solution was then evaporated under reduced pressure. The resulting oil was dissolved in a minimum amount of hot benzene. Ligroin was added to the latter mixture until the solution became cloudy, whereupon the solution was reheated and left to stand overnight in a refrigerator. Upon standing overnight, colorless to light yellow crystals of 6-(methylthio)-chroman-4-one formed having a melting point 34°–36° C.

PREPARATION C

A mixture consisting of 6-(methylthio)-chroman-4-one, (12 g, 62 mmol) potassium cyanide (6 g 92 mmol) ammonium carbonate (12 g 125 mmol) in 65 ml of 90% ethanol was sealed in a glass reactor and heated to 95°–100° C. for 18 hours. The cooled reactive mixture was poured into 100 c.c. of ice water containing 10 ml. of conc. hydrochloric acid. The resulting slurry was extracted with ethyl acetate and benzene (9:1) with one teaspoon of activated charcoal and 100 g of anhydrous sodium sulfate being added thereto and filtered therefrom with an ethyl acetate wash. The dried organic solution was then extracted with dilute (5%) sodium hydroxide. The aqueous washings of the organic solution were acidified with cold dilute acid. The resulting solid was collected, washed with water and dried. The desired dl-spiro-(6-methylthio-chroman-4,4'-imidazolidine)-2',5'-dione was obtained as a white solid with a melting point of 193°–195° C. dec. in a 98% yield (16.0 g); HRMS for C$_{12}$H$_{12}$N$_2$O$_3$S calc. 264.0568, obs. 264.0571, 0.3 mmu/1.1 ppm; elemental analysis for C$_{12}$H$_{12}$N$_2$O$_3$S calc. %C 54.53 %H 4.58 %N 10.61, obs. %C 54.62 %H 4.66 %N 10.46, obs. %C 54.72 %H 4.66 %N 10.38.

PREPARATION D dl-Spiro-(6-methylthio-chroman-4,4'-imidazolidine)-2',5'-dione (4.0 g 150 mmol) was added to sodium periodate (3.5 g) in 50% methanol (600 ml). The mixture was stirred at room temperature for 16 hours than acidified (pH 4) and extracted with ethyl acetate. The combined organic extracts were dried over anhydrous sodium sulfate and the solvent removed under reduced pressure. The resulting solid was triturated with ether and collected to afford 3.9 gm (92% ) the diastereomeric mixture of spiro-(6-methylsulfinyl chroman-4,4'-imidazolidine)-2',5'-dione with a melting point of 240°–243° C. dec.; HRMS for C$_{12}$H$_{12}$N$_2$O$_4$S calc. 280.0518, error 0.7 mmu/2.5 ppm, obs. 280.0525.

The spiro-hydantoin compounds of Preparations C and D were tested for their ability to reduce or inhibit aldose reductase enzyme activity via the procedures of P. F. Kador et. al. as described in Biophysical Chemistry, 8 (1978) 81–85 and P. F. Kador et. al. as described in Documenta Ophthamologica, 18 (1979) 117. In every case the substrate employed was partially purified aldose reductase enzyme obtained from rat lens or human placenta.

| COMPOUND | IC$_{50}$* RAT | HUMAN |
|---|---|---|
| C | 2.7 × 10$^{-7}$M | 6.6 × 10$^{-7}$M |
| D |  | 1.2 × 10$^{-5}$M |
| SARGES** | 2.7 × 10$^{-7}$M | 6.4 × 10$^{-7}$M |
| SARGES*** | 6.1 × 10$^{-7}$M | 1.4 × 10$^{-6}$M |

*IC$_{50}$ = Concentration of drug that inhibits 50% of the enzyme activity.
**Sarges Compound = d-spiro (6-fluoro-chroman-4,4'-imidazolidine)-2',5'-dione.
***Sarges Compound = dl-spiro-(6-fluoro-chroman-4,'-imidazolidine)-2',5'-dione (racemic).

The effect of the 6-methylthio and 6-methylsulfoxide spiro-chroman imidazolidine on the prevention or retardation of cataracts in rats was studied using the resolved d-6-fluoro spiro imidazolidine based upon U.S. Pat. No. 4,130,714. The compounds to be tested were:
1. Spiro [6-methylthio-chroman-4,4'-imidazolidine]-2',5'-dione
2. Spiro [6-methylthio-chroman-4,4'-imidazolidine]-2',5'-dione sulfoxide
3. d-Spiro [6-fluorochroman-4,4'-imidazolidine]-2',5'-dione.

Test compound/diet mixtures were formulated as follows:

| Test Compound | Free Compound (%) | Galactose |
|---|---|---|
| A. methylthio (racemic) | 0.0025 | 30.00 |
| B. methylthio (racemic) | 0.01 | 30.00 |
| C. methylsulfinyl (diastereomeric mixture) | 0.0025 | 30.00 |
| D. methylsulfinyl (diastereomeric mixture) | 0.01 | 30.00 |
| E. d-6-fluoro | 0.0025 | 30.00 |
| control (Galactose) | — |  |

The feed used for dilution to 100% was Purina Rodent Laboratory Chow, Number 5001, pelleted, which was ground. The test compounds at the 0.0025% level was designed to provide a 5 mg per kilogram per day intake starting with 50 gram rats. Similarly, the 0.01% level was designed to provide a drug concentration of 20 mg per kilogram per day.

All animals were fed the Purina Laboratory Chow and water, ad libitum for a two day acclimatization period. The indicated test compound/diet mixture then was introduced to all animals on Study Day 1 and the animals were maintained on this diet throughout thirty days of the study.

Sufficient amounts of test compound/diet mixture were maintained in the food hoppers to allow the animals to eat ad libitum. All aliquots of test compound/diet mixture added to the food hoopers were weighed and the weights, as well as day of addition, recorded.

Twelve animals were assigned to each treatment with each compound at the indicated percentage by total weight of feed. All eyes were examined with a handheld ophthalmoscope and/or penlight. Each eye was given one of the following grades:

| Grade | Description |
|---|---|
| Normal | — | Normal lens, no visible vacuoles or opacities |
| Time to vacuole | + | Vacuolization visible on anterior lens surface |
| Time to snowflake | S | Small opaque "flecks" and vacuoles |
| Time to nuclear cataract | N | Nuclear cataract; interior lens opaque |

The data obtained is set forth in the following Table.

| Study Days | Test Compound | Number of Eyes | | | | | % of Total Eyes Observed | | | |
|---|---|---|---|---|---|---|---|---|---|---|
| | | — | ± | + | S | N | — | + | S | N |
| 2 | A | 24 | 0 | 0 | 0 | 0 | 100.0 | 0 | 0 | 0 |
| | B | 24 | 0 | 0 | 0 | 0 | 100.0 | 0 | 0 | 0 |
| | C | 24 | 0 | 0 | 0 | 0 | 100.0 | 0 | 0 | 0 |
| | D | 24 | 0 | 0 | 0 | 0 | 100.0 | 0 | 0 | 0 |
| | E | 24 | 0 | 0 | 0 | 0 | 100.0 | 0 | 0 | 0 |
| | Control | 24 | 0 | 0 | 0 | 0 | 100.0 | 0 | 0 | 0 |
| 3 | A | 24 | 0 | 0 | 0 | 0 | 100.0 | 0 | 0 | 0 |
| | B | 24 | 0 | 0 | 0 | 0 | 100.0 | 0 | 0 | 0 |
| | C | 24 | 0 | 0 | 0 | 0 | 100.0 | 0 | 0 | 0 |
| | D | 22 | 2 | 0 | 0 | 0 | 91.7 | 0 | 0 | 0 |
| | E | 24 | 0 | 0 | 0 | 0 | 100.0 | 0 | 0 | 0 |
| | Control | 20 | 4 | 0 | 0 | 0 | 83.3 | 0 | 0 | 0 |
| 4 | A | 19 | 5 | 0 | 0 | 0 | 79.2 | 0 | 0 | 0 |
| | B | 24 | 0 | 0 | 0 | 0 | 100.0 | 0 | 0 | 0 |
| | C | 4 | 20 | 0 | 0 | 0 | 16.7 | 0 | 0 | 0 |
| | D | 18 | 2 | 4 | 0 | 0 | 75.0 | 16.7 | 0 | 0 |
| | E | 24 | 0 | 0 | 0 | 0 | 100.0 | 0 | 0 | 0 |
| | Control | 13 | 5 | 6 | 0 | 0 | 54.2 | 25.0 | 0 | 0 |
| 5 | A | 2 | 18 | 4 | 0 | 0 | 8.3 | 16.7 | 0 | 0 |
| | B | 22 | 2 | 0 | 0 | 0 | 91.7 | 0 | 0 | 0 |
| | C | 0 | 6 | 18 | 0 | 0 | 0 | 75.0 | 0 | 0 |
| | D | 8 | 8 | 8 | 0 | 0 | 33.3 | 33.3 | 0 | 0 |
| | E | 24 | 0 | 0 | 0 | 0 | 100.0 | 0 | 0 | 0 |
| | Control | 0 | 10 | 14 | 0 | 0 | 0 | 58.4 | 0 | 0 |
| 6 | A | 2 | 8 | 14 | 0 | 0 | 8.3 | 58.4 | 0 | 0 |
| | B | 15 | 9 | 0 | 0 | 0 | 62.5 | 0 | 0 | 0 |
| | C | 0 | 4 | 20 | 0 | 0 | 0 | 83.3 | 0 | 0 |
| | D | 6 | 8 | 10 | 0 | 0 | 25.0 | 41.6 | 0 | 0 |
| | E | 24 | 0 | 0 | 0 | 0 | 100.0 | 0 | 0 | 0 |
| | Control | 0 | 2 | 22 | 0 | 0 | 0 | 91.7 | 0 | 0 |
| 8 | A | 2 | 6 | 16 | 0 | 0 | 8.3 | 66.7 | 0 | 0 |
| | B | 10 | 12 | 2 | 0 | 0 | 41.6 | 8.3 | 0 | 0 |
| | C | 0 | 0 | 24 | 0 | 0 | 0 | 100.0 | 0 | 0 |
| | D | 4 | 6 | 12 | 2 | 0 | 16.7 | 50.0 | 8.3 | 0 |
| | E | 24 | 0 | 0 | 0 | 0 | 100.0 | 0 | 0 | 0 |
| | Control | 0 | 0 | 22 | 2 | 0 | 0 | 91.7 | 8.3 | 0 |
| 10 | A | 2 | 4 | 15 | 3 | 0 | 8.3 | 62.5 | 12.5 | 0 |
| | B | 9 | 9 | 6 | 0 | 0 | 37.5 | 25.0 | 0 | 0 |
| | C | 0 | 0 | 19 | 5 | 0 | 0 | 79.2 | 20.8 | 0 |
| | D | 2 | 4 | 14 | 4 | 0 | 8.3 | 58.4 | 16.7 | 0 |
| | E | 24 | 0 | 0 | 0 | 0 | 100.0 | 0 | 0 | 0 |
| | Control | 0 | 0 | 16 | 8 | 0 | 0 | 66.7 | 33.3 | 0 |
| 12 | A | 0 | 3 | 17 | 4 | 0 | 0 | 70.8 | 16.7 | 0 |
| | B | 7 | 7 | 10 | 0 | 0 | 29.2 | 41.6 | 0 | 0 |
| | C | 0 | 0 | 14 | 10 | 0 | 0 | 58.4 | 41.6 | 0 |
| | D | 0 | 4 | 15 | 5 | 0 | 0 | 62.5 | 20.8 | 0 |
| | E | 23 | 1 | 0 | 0 | 0 | 95.8 | 0 | 0 | 0 |
| | Control | 0 | 0 | 11 | 13 | 0 | 0 | 45.8 | 54.2 | 0 |
| 14 | A | 0 | 1 | 16 | 7 | 0 | 0 | 66.7 | 29.2 | 0 |
| | B | 3 | 3 | 18 | 0 | 0 | 12.5 | 78.0 | 0 | 0 |
| | C | 0 | 0 | 10 | 14 | 0 | 0 | 41.6 | 58.4 | 0 |
| | D | 0 | 2 | 15 | 7 | 0 | 0 | 62.5 | 29.2 | 0 |
| | E | 21 | 3 | 0 | 0 | 0 | 87.5 | 0 | 0 | 0 |
| | Control | 0 | 0 | 5 | 19 | 0 | 0 | 20.8 | 79.2 | 0 |
| 16 | A | 0 | 0 | 12 | 12 | 0 | 0 | 50.0 | 50.0 | 0 |
| | B | 0 | 4 | 20 | 0 | 0 | 0 | 83.3 | 0 | 0 |
| | C | 0 | 0 | 9 | 15 | 0 | 0 | 37.5 | 62.5 | 0 |
| | D | 0 | 2 | 13 | 9 | 0 | 0 | 45.8 | 37.5 | 0 |
| | E | 20 | 4 | 0 | 0 | 0 | 83.3 | 0 | 0 | 0 |
| | Control | 0 | 0 | 4 | 20 | 0 | 0 | 16.7 | 83.3 | 0 |
| 18 | A | 0 | 0 | 8 | 16 | 0 | 0 | 33.3 | 66.7 | 0 |
| | B | 0 | 1 | 23 | 0 | 0 | 0 | 95.8 | 0 | 0 |
| | C | 0 | 0 | 6 | 0 | 0 | 0 | 25.0 | 75.0 | 0 |
| | D | 0 | 2 | 13 | 9 | 0 | 0 | 54.2 | 37.5 | 0 |
| | E | 14 | 10 | 0 | 0 | 0 | 58.4 | 0 | 0 | 0 |
| | Control | 0 | 0 | 4 | 18 | 2 | 0 | 16.7 | 75.0 | 8.3 |
| 20 | A | 0 | 0 | 6 | 18 | 0 | 0 | 25.0 | 75.0 | 0 |
| | B | 0 | 1 | 22 | 1 | 0 | 0 | 91.7 | 4.2 | 0 |
| | C | 0 | 0 | 5 | 19 | 0 | 0 | 20.8 | 79.2 | 0 |

-continued

| Study Days | Test Compound | Number of Eyes | | | | | % of Total Eyes Observed | | | |
|---|---|---|---|---|---|---|---|---|---|---|
| | | − | ± | + | S | N | − | + | S | N |
| | D | 0 | 2 | 7 | 14 | 1 | 0 | 29.2 | 58.4 | 4.2 |
| | E | 3 | 10 | 1 | 10 | 0 | 12.5 | 4.2 | 41.6 | 0 |
| | Control | 0 | 0 | 3 | 16 | 5 | 0 | 12.5 | 66.7 | 20.8 |
| 22 | A | 0 | 0 | 6 | 18 | 0 | 0 | 25.0 | 75.0 | 0 |
| | B | 0 | 0 | 17 | 7 | 0 | 0 | 70.8 | 29.2 | 0 |
| | C | 0 | 0 | 2 | 21 | 1 | 0 | 8.3 | 87.5 | 4.2 |
| | D | 0 | 0 | 5 | 17 | 2 | 0 | 20.8 | 70.8 | 8.3 |
| | E | 0 | 6 | 2 | 16 | 0 | 0 | 8.3 | 66.7 | 0 |
| | Control | 0 | 0 | 0 | 17 | 7 | 0 | 0 | 70.8 | 29.2 |
| 24 | A | 0 | 0 | 4 | 20 | 0 | 0 | 16.7 | 83.3 | 0 |
| | B | 0 | 0 | 11 | 13 | 0 | 0 | 45.8 | 54.2 | 0 |
| | C | 0 | 0 | 1 | 22 | 1 | 0 | 4.2 | 91.7 | 4.2 |
| | D | 0 | 0 | 5 | 17 | 2 | 0 | 20.8 | 70.8 | 8.3 |
| | E | 0 | 1 | 3 | 20 | 0 | 0 | 12.5 | 83.3 | 0 |
| | Control | 0 | 0 | 0 | 16 | 8 | 0 | 0 | 66.7 | 33.3 |
| 26 | A | 0 | 0 | 2 | 22 | 0 | 0 | 8.3 | 91.7 | 0 |
| | B | 0 | 0 | 5 | 19 | 0 | 0 | 20.8 | 79.2 | 0 |
| | C | 0 | 0 | 0 | 23 | 1 | 0 | 0 | 95.8 | 4.2 |
| | D | 0 | 0 | 4 | 18 | 2 | 0 | 16.7 | 75.0 | 8.3 |
| | E | 0 | 0 | 4 | 20 | 0 | 0 | 16.7 | 83.3 | 0 |
| | Control | 0 | 0 | 0 | 14 | 10 | 0 | 0 | 58.3 | 41.7 |
| 28 | A | 0 | 0 | 2 | 20 | 2 | 0 | 8.3 | 83.3 | 8.3 |
| | B | 0 | 0 | 2 | 22 | 0 | 0 | 8.3 | 91.7 | 0 |
| | C | 0 | 0 | 0 | 21 | 3 | 0 | 0 | 87.5 | 12.5 |
| | D | 0 | 0 | 4 | 16 | 4 | 0 | 16.7 | 66.7 | 16.7 |
| | E | 0 | 0 | 2 | 22 | 0 | 0 | 8.3 | 91.7 | 0 |
| | Control | 0 | 0 | 0 | 12 | 12 | 0 | 0 | 50.0 | 50.0 |
| 30 | A | 0 | 0 | 1 | 20 | 3 | 0 | 4.2 | 83.3 | 12.5 |
| | B | 0 | 0 | 1 | 23 | 0 | 0 | 4.2 | 95.8 | 0 |
| | C | 0 | 0 | 0 | 20 | 4 | 0 | 0 | 83.3 | 16.7 |
| | D | 0 | 0 | 1 | 19 | 4 | 0 | 4.2 | 79.2 | 16.7 |
| | E | 0 | 0 | 1 | 23 | 0 | 0 | 4.2 | 95.8 | 0 |
| | Control | 0 | 0 | 0 | 11 | 13 | 0 | 0 | 45.8 | 54.2 |

A = Racemic 6-methylthio derivative at 0.0025%
B = Racemic 6-methylthio derivative at 0.01%
C = Diastereomeric 6-methylsulfinyl derivative at 0.0025%
D = Disastereomeric 6-methylsulfinyl derivative at 0.01%
E = d-6-Fluoro derivative (Sarges) at 0.0025%

Time to Vacuole

The 0.0025% methylthio compound which was equal to the galactose control was significantly different from control in the "time to vacuole formation". The status of the 0.0025% methylthio compound and 0.01% sulfinyl derivative are not different from each other, but are different (p<0.05) from control.

The 0.01% methylthio compound when compared to its 0.0025% d-6-fluoro equivalent was found to be statistically lower (p<0.05) than the Sarges standard. The ratio of the time of suppression between the 0.0025% d-6-fluoro compound and 0.01% methylthio compound was 1.5:1 (20.8:13.5 days), respectively, for the "time to vacuole formation".

Time to Snowflake

The 0.01% methylthio compound was not significantly different from the Sarges 0.0025% d-6-fluoro control. However, the 0.01% methylthio compound did retard the progress of cataract formation slightly better than the Sarges control. Again the progress of retardation of cataract by the 0.01% methylthio compound increased and continued to increase with time and as shown here surpassed the positive control.

Time to Nuclear Cataract

Both the 0.01% methylthio and Sarges 0.0025% d-6-fluoro compound suppress by 100% the formation of nuclear cataracts for periods of 30 days. The 0.0025% sufinyl, the 0.01% sulfinyl and the 0.0025% methylthio compounds showed greater than 80% suppression in the same time period. The compounds tested herein have the ability to suppress this advanced stage of cataract formation.

This study shows that the inhibitory capacities follow the order d-6-fluoro derivative to be 1.5 times greater than the racemic 6-methylthio derivative which is 1.5 greater than the diastereomeric mixture of the 6-sulfinyl derivative.

The methylthio compound, however, has significant advantages over the resolved 6-fluoro compound. To attain its marginally increased inhibitory capacity, the d-6-fluoro compound has to be resolved whereas the 6-methylthio compound is the less expensive racemate. The biotransformation of the methylthio compound to the sulfoxide and the latter compound's conversion to the methylthio compound provides a dynamic metabolic buffering system to reduce potential toxicity effects of the compounds on chronic use. The 6-methylthio derivative can through resolution of the racemate be increased as much as 2 times in potency. The 6-methylsulfinyl derivative by virtue of containing two chiral centers can be resolved to yield an inhibitor activity of up to 4 times its diastereomeric mixture activity. Finally, the further oxidation of the sulfoxide to sulfone provides another route of metabolism and drug disposition to reduce potential toxicity of either drug.

It should be understood that while certain preferred embodiments of the present invention have been illustrated and described, various modifications thereof will become apparent to those skilled in the art. Accord-

What is claimed is:

1. A compound of the formula:

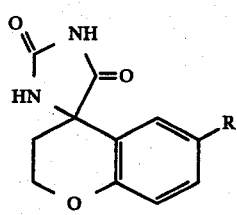

or a pharmacologically acceptable salt thereof where R=CH$_3$S and CH$_3$S(O)—.

2. A compound as recited in claim 1 wherein R=CH$_3$S(O).

3. A method for treatment of mammals suffering from diabetic complications comprising orally administering an effective amount of spiro-chroman-imidazolidine having the formula

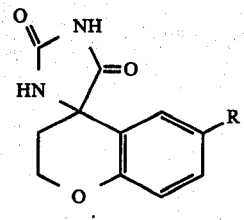

or a pharmaceutically acceptable salt thereof where R=CH$_3$S— and CH$_3$S(O)—.

4. A method as recited in claim 3 wherein R=CH$_3$S(O)—.

* * * * *